US011937947B2

United States Patent
Chen

(10) Patent No.: US 11,937,947 B2
(45) Date of Patent: Mar. 26, 2024

(54) LOW-NOISE BIOPOTENTIAL ACQUISITION SYSTEM FOR DRY ELECTRODE APPLICATION

(71) Applicant: MEDIATEK INC., Hsin-Chu (TW)

(72) Inventor: Chih-Hsin Chen, Hsinchu (TW)

(73) Assignee: MEDIATEK INC., Hsin-Chu (TW)

( * ) Notice: Subject to any disclaimer, the term of this patent is extended or adjusted under 35 U.S.C. 154(b) by 58 days.

(21) Appl. No.: 17/219,910

(22) Filed: Apr. 1, 2021

(65) Prior Publication Data

US 2021/0330267 A1 Oct. 28, 2021

Related U.S. Application Data

(60) Provisional application No. 63/014,749, filed on Apr. 24, 2020.

(51) Int. Cl.
*A61B 5/00* (2006.01)

(52) U.S. Cl.
CPC .................. *A61B 5/7221* (2013.01)

(58) Field of Classification Search
CPC .................................................. A61B 5/7221
USPC ......................................................... 600/301
See application file for complete search history.

(56) References Cited

U.S. PATENT DOCUMENTS 5,861,013 A * 1/1999 Peck ...................... A61N 1/371
607/28

| 2015/0119747 A1* | 4/2015 | Torfs ...................... A61B 5/053 600/547 |
| 2016/0183813 A1* | 6/2016 | Naima .................. A61B 5/0537 600/479 |
| 2019/0160291 A1* | 5/2019 | Peichel ................ A61N 1/3962 |

FOREIGN PATENT DOCUMENTS

| CN | 104825154 A | 8/2015 |
| TW | 202023474 A | 7/2020 |

OTHER PUBLICATIONS

Sunyoung Kim, "A 2.4uA Continuous-time Electrode-Skin Impedance Measurement Circuit for Motion Artifact Monitoring in ECG Acquisition Systems", 2010 Symposium on VLSI Circuits/ Technical Digest of Technical Papers.

Nick Van Helleputte, "A 160 uA Biopotential Acquisition IC With Fully Integrated IA and Motion Artifact Suppression", IEEE Transactions on Biomedical Circuits and Systems, vol. 6, No. 6, Dec. 2012.

Nick Van Helleputte, "A Multi-Parameter Signal-Acquisition SoC for Connected Personal Health Applications", 2014 IEEE International Solid-State Circuits Conference.

* cited by examiner

*Primary Examiner* — Nicole F Lavert
(74) *Attorney, Agent, or Firm* — Winston Hsu

(57) ABSTRACT

The present invention provides a circuitry of a biopotential acquisition system, where the circuitry includes an input node, an ETI transmitter, a capacitor and an ETI receiver. The input node is configured to receive an input signal from an electrode of the biopotential acquisition system. The ETI transmitter is configured to generate a transmitter signal. A first node of the capacitor is coupled to the ETI transmitter, and a second node of the capacitor is coupled to the input node. The ETI receiver is coupled to the input node, and is configured to receive the transmitter signal via the capacitor to generate an ETI.

9 Claims, 5 Drawing Sheets

LOW-NOISE BIOPOTENTIAL ACQUISITION SYSTEM FOR DRY ELECTRODE APPLICATION

CROSS REFERENCE TO RELATED APPLICATIONS

This application claims the priority of U.S. Provisional Application No. 63/014,749, filed on Apr. 24, 2020, which is included herein by reference in its entirety.

BACKGROUND

A conventional medical device generally uses large dry electrodes or wet electrodes to measure physiological signals to obtain physiological features such as bio-impedance or electrocardiography. Recently, personal biosensors such as portable/wearable medical devices become popular for providing physiological information at all time for the reference to the user. Considering the use and design of these portable medical devices, smaller dry electrodes are more appropriate. However, smaller dry electrode means worse electrode impedance, and the worse electrode impedance (i.e. large electrode impedance) may cause detection error of electrocardiography (ECG) signals. In addition, because an electrode-tissue impedance (ETI) may change greatly due to contact factors or motion artifact, it increases the difficulty of measuring ECG signals.

To solve the problem of the ECG signals in the dry electrode application, the ETI is also detected to reduce the motion artifact in the ECG signals. In the conventional art, a current for the ETI measurement is injected into the electrodes, and an ETI receiver detects the voltages at the electrodes to determine the ETI. However, injecting the current into the electrodes of the conventional art may induce additional noise to the electrodes, causing detection error of the ECG signals. In addition, because the current generator having lower impedance is connected to the electrodes, strength of the ECG signals may be influenced, and an input range for the ECG signals becomes narrow.

SUMMARY

It is therefore an objective of the present invention to provide a biopotential acquisition system, which can accurately measure the ECG signals while measuring the ETI, to solve the above-mentioned problems.

According to one embodiment of the present invention, a circuitry of a biopotential acquisition system is disclosed. The circuitry comprises an input node, an ETI transmitter, a capacitor and an ETI receiver. The input node is configured to receive an input signal from an electrode of the biopotential acquisition system. The ETI transmitter is configured to generate a transmitter signal. A first node of the capacitor is coupled to the ETI transmitter, and a second node of the capacitor is coupled to the input node. The ETI receiver is coupled to the input node, and is configured to receive the transmitter signal via the capacitor to generate an ETI.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the following description and claims to refer to particular system components. As one skilled in the art will appreciate, manufacturers may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". The terms "couple" and "couples" are intended to mean either an indirect or a direct electrical connection. Thus, if a first device couples to a second device, that connection may be through a direct electrical connection, or through an indirect electrical connection via other devices and connections.

Figure 1:
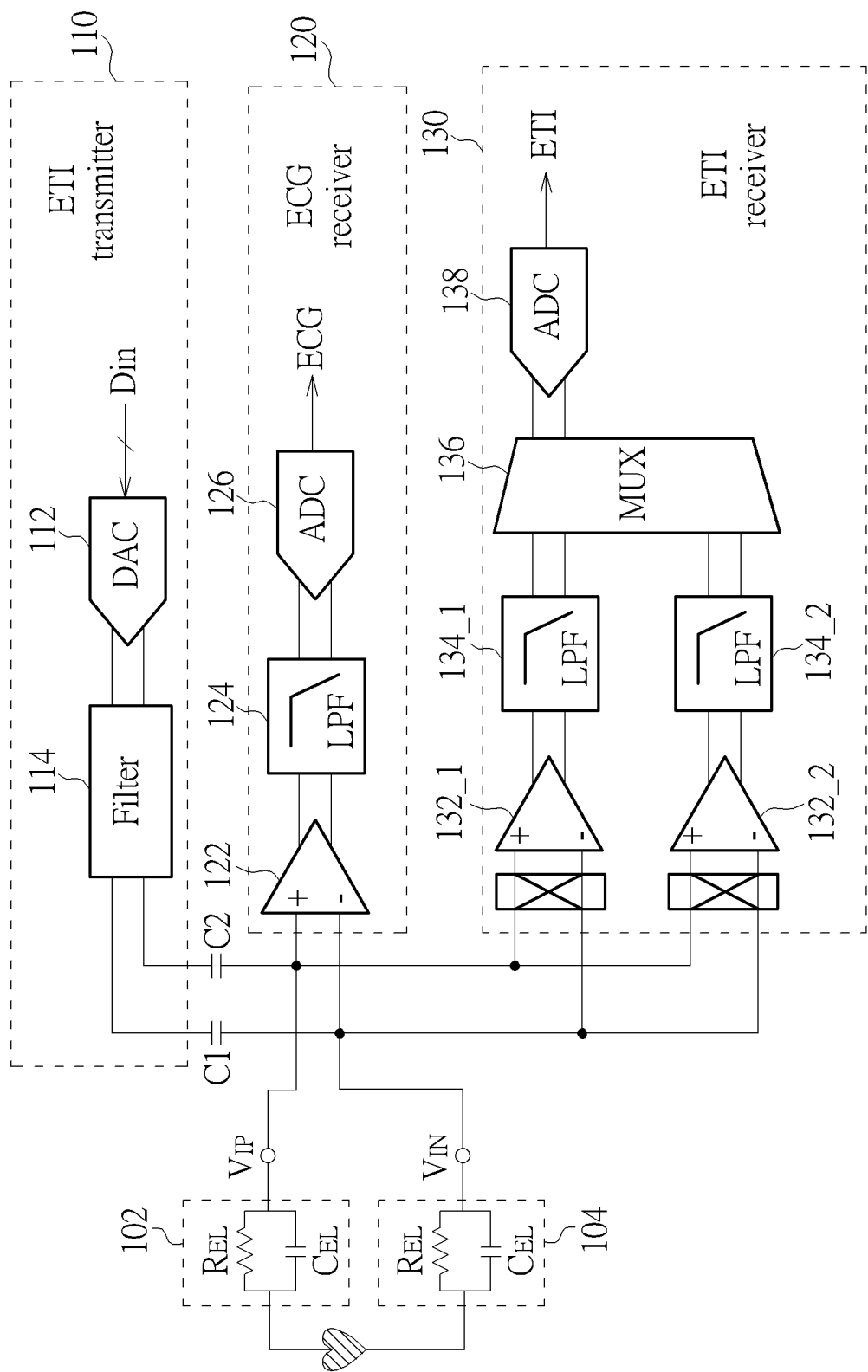
FIG. 1 is a diagram illustrating a biopotential acquisition system 100 according to one embodiment of the present invention.

FIG. 1 is a diagram illustrating a biopotential acquisition system 100 according to one embodiment of the present invention. As shown in FIG. 1, the biopotential acquisition system 100 is a two-electrode biopotential acquisition system having two electrodes 102 and 104, and the electrodes 102 and 104 are used to connect to a right body (e.g., right hand) and a left body (e.g., left hand) to obtain biopotential signals of a human body, and the biopotential acquisition system 100 can process and analyze the biopotential signals to determine physiological signals such as electrocardiography (ECG) signals, and the physiological features can be displayed on a screen of the biopotential acquisition system 100. In this embodiment, the biopotential acquisition system 100 can be built in any portable electronic device or a wearable electronic device.

The biopotential acquisition system 100 comprises an ETI transmitter 110, an ECG receiver 120 and an ETI receiver 130, wherein the ETI transmitter 110 comprises a digital-to-analog converter (DAC) 112 and a filter 114; the ECG receiver 120 comprises a low-noise amplifier 122, a low-pass filter (LPF) 124 and an analog-to-digital converter (ADC) 126; and the ETI receiver 130 comprises a first amplifier with mixer 132_1, a second amplifier with mixer 132_2, a first low-pass filter 134_1, a second low-pass filter 134_2, a multiplexer 136 and an ADC 138. In addition, the biopotential acquisition system 100 further comprises a first capacitor C1 and a second capacitor C2, wherein a first node of the first capacitor C1 is coupled to the filter 114, and a second node of the first capacitor C1 is coupled to one input node of the biopotential acquisition system 100 (i.e. the second node is coupled to the electrode 104 and the negative input terminal of the low-noise amplifier 122); and a first node of the second capacitor C2 is coupled to the filter 114, and a second node of the second capacitor C2 is coupled to another input node of the biopotential acquisition system 100 (i.e. the second node is coupled to the electrode 102 and the positive input terminal of the low-noise amplifier 122).

When the electrodes 102 and 104 are connected to the human body, the ETI is formed so that the biopotential acquisition system 100 may have large input impedance, and the input impedance may change greatly due to contact factors or motion artifact. In the embodiment shown in FIG. 1 the ETI with the impedance of the electrode 102/104 are modeled as a resistor $R_{EL}$ and a capacitor $C_{EL}$ connected in parallel. In the operation of the biopotential acquisition system 100, when the electrodes 102 and 104 are in contact with the human body and the biopotential acquisition system 100 starts to measure the ECG signals, the low-noise amplifier 122 of the ECG receiver 120 starts to receive input signals $V_{IP}$ and $V_{IN}$ (biopotential signals) from the electrodes 102 and 104 to generate an amplified signal, and the amplified signal is processed by the low-pass filter 124 and the ADC 126 to determine the physiological information such as the ECG signals. At this time, because the input impedance (i.e., $R_{EL}$ and $C_{EL}$) may change greatly due to the motion artifact, the ECG signals may not be accurate. Therefore, in order to solve the ETI problem, meanwhile, the ETI transmitter 110 and the ETI receiver 130 are controlled to determine the ETI, for the biopotential acquisition system 100 to notify the user about the motion artifact issue or to adjust/compensate the ECG signals generated by the ECG receiver 120.

Figure 2:
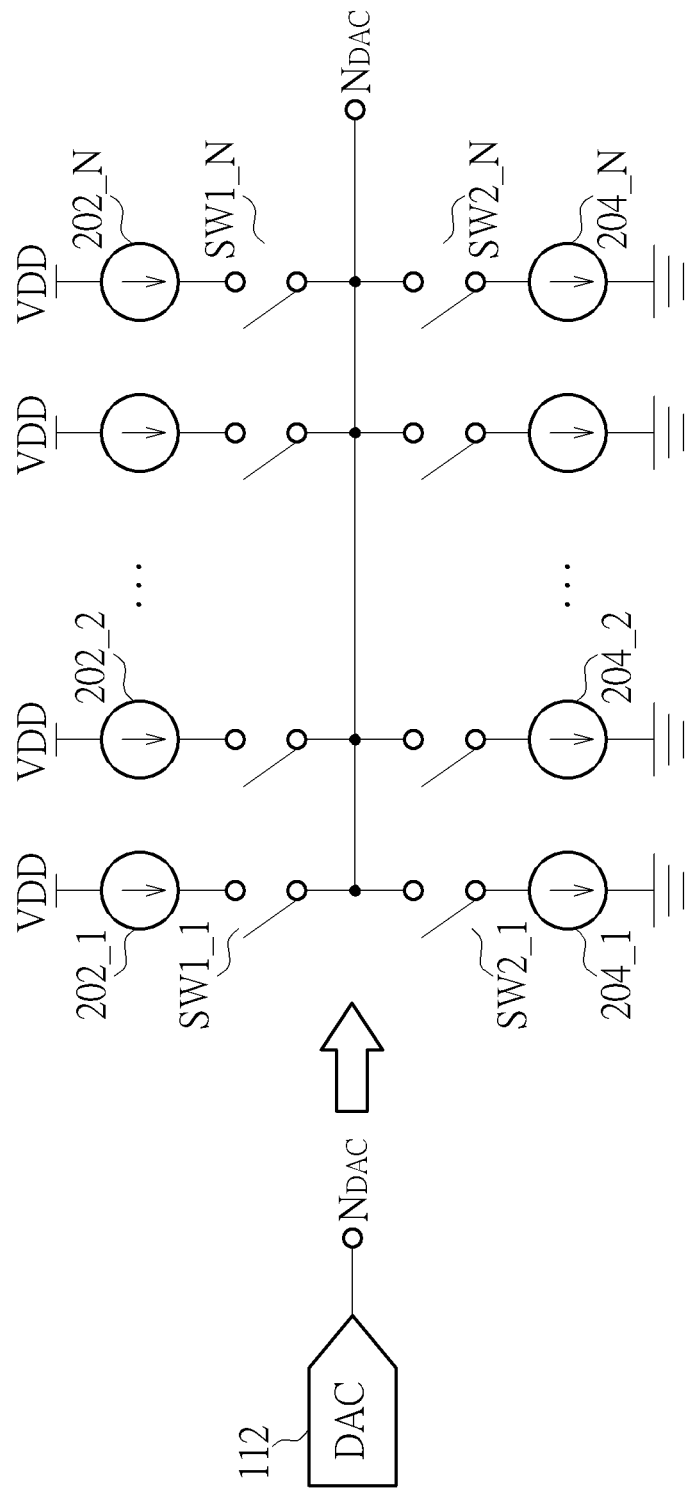
FIG. 2 shows a current DAC according to one embodiment of the present invention.
Figure 3:
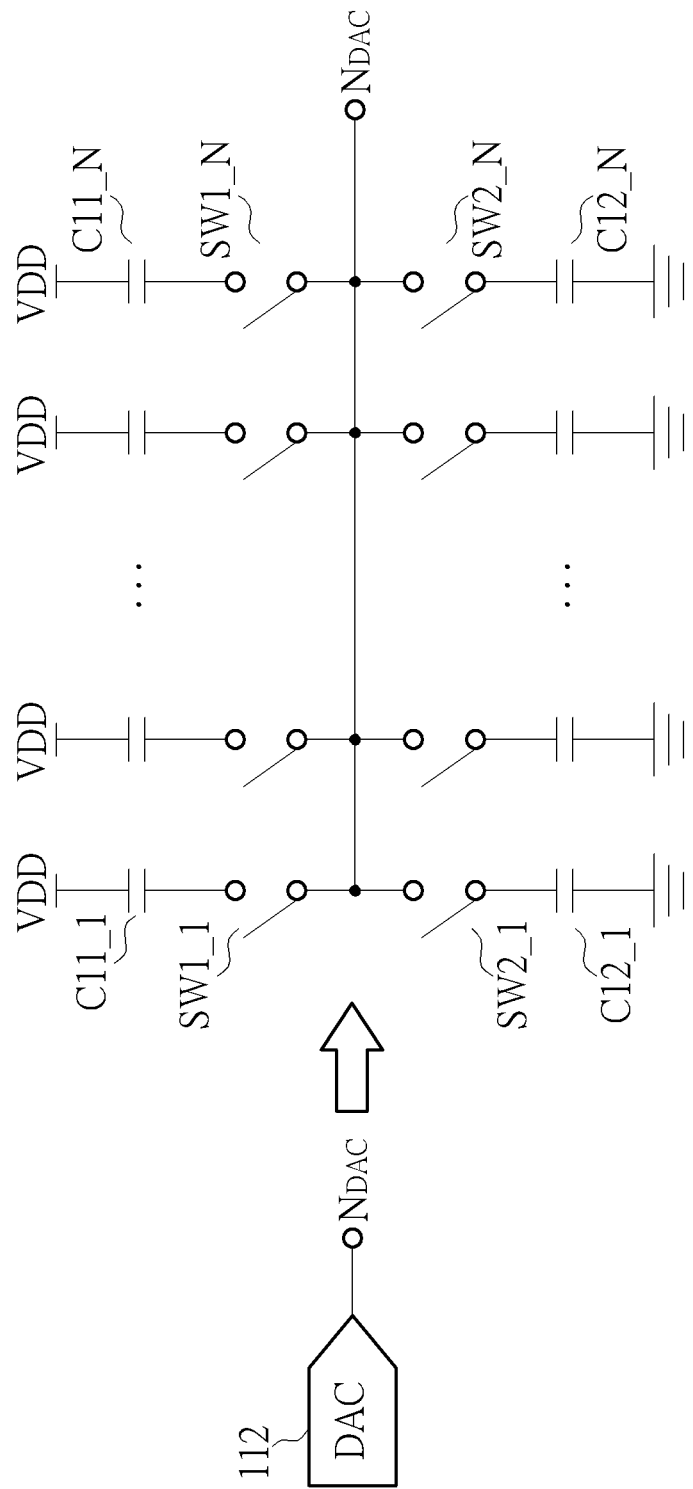
FIG. 3 shows a capacitor DAC according to one embodiment of the present invention.
Figure 4:
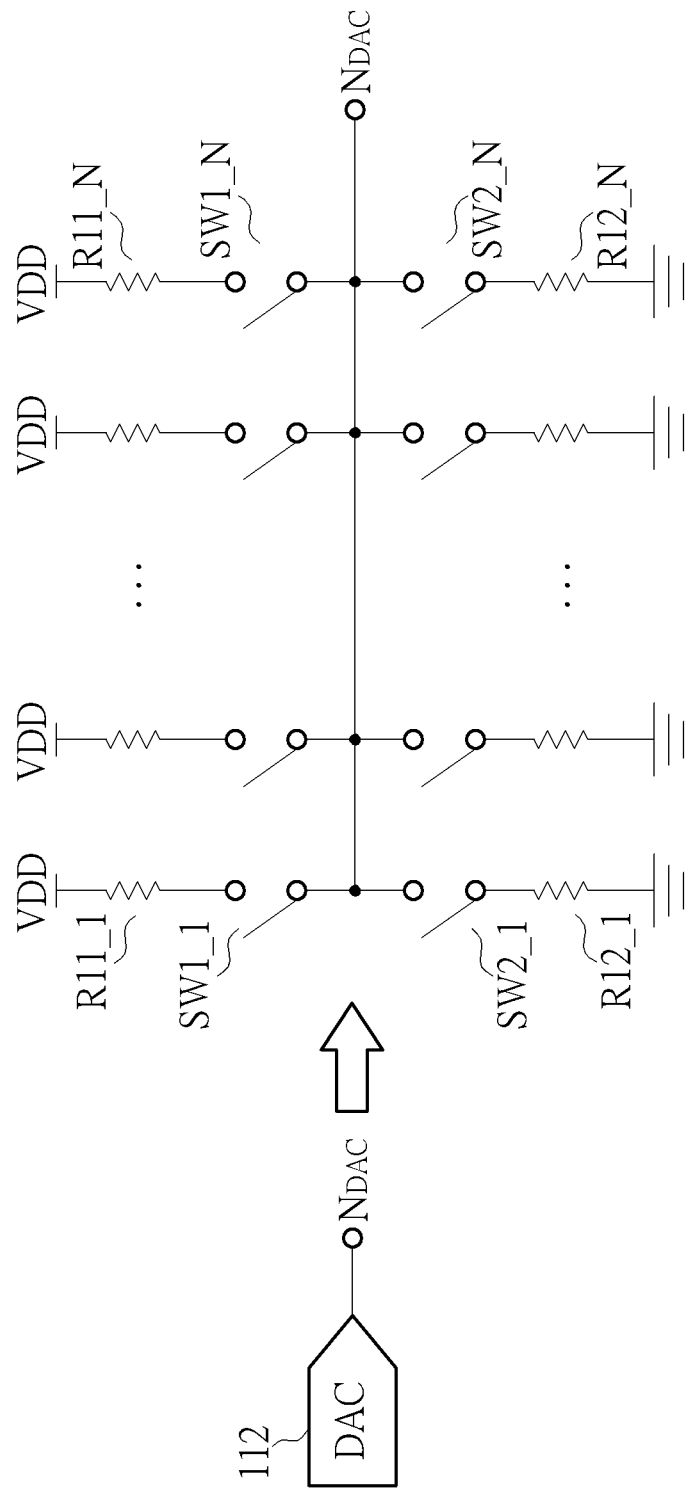
FIG. 4 shows a resistor DAC according to one embodiment of the present invention.

Regarding the operation of the ETI transmitter 110, the DAC 112 receives a digital input signal Din to generate a transmitter signal, wherein the DAC 112 can be implemented by any suitable DAC such as a current DAC, a capacitor DAC or a resistor DAC. FIG. 2 shows a current DAC according to one embodiment of the present invention, wherein the current DAC comprises a plurality of current sources 202_1-202_N and a plurality of current sources 204_1-204_N, the plurality of current sources 202_1-202_N are selectively connected to an output node $N_{DAC}$ of the DAC 112 via a plurality of switches SW1_1-SW1_N, and the plurality of current sources 204_1-204_N are selectively connected to the output node $N_{DAC}$ of the DAC 112 via a plurality of switches SW2_1-SW2_N. FIG. 3 shows a capacitor DAC according to one embodiment of the present invention, wherein the capacitor DAC comprises a plurality of capacitors C11_1-C11_N and a plurality of C12_1-C12_N, the plurality of capacitors C11_1-C11_N are selectively connected to an output node $N_{DAC}$ of the DAC 112 via a plurality of switches SW1_1-SW1_N, and the plurality of capacitors C11_1-C11_N are selectively connected to the output node $N_{DAC}$ of the DAC 112 via a plurality of switches SW2_1-SW2_N. FIG. 4 shows a resistor DAC according to one embodiment of the present invention, wherein the resistor DAC comprises a plurality of resistors R11_1-R11_N and a plurality of resistors R12_1-R12_N, the plurality of resistors R11_1-R11_N are selectively connected to an output node $N_{DAC}$ of the DAC 112 via a plurality of switches SW1_1-SW1_N, and the plurality of resistors R12_1-R12_N are selectively connected to the output node $N_{DAC}$ of the DAC 112 via a plurality of switches SW2_1-SW2_N.

In this embodiment, a frequency of the transmitter signal generated by the DAC 112 is higher than the ECG signals. For example, the ECG signals may have frequency lower than several hundred hertz, but the transmitter signal generated by the DAC 112 may be several kilohertz.

Figure 5:
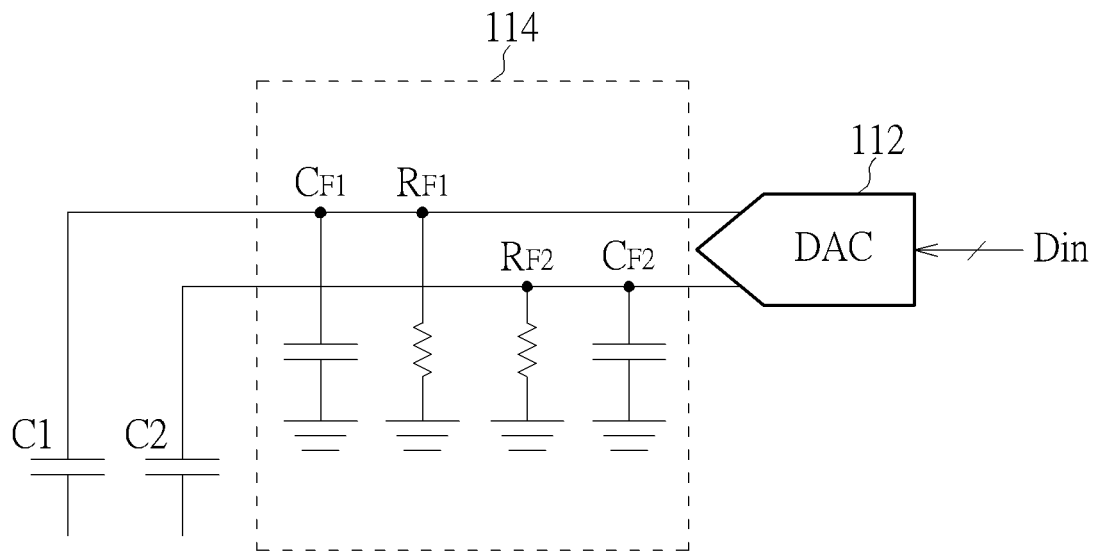
FIG. 5 shows a passive filter according to one embodiment of the present invention.
Figure 6:
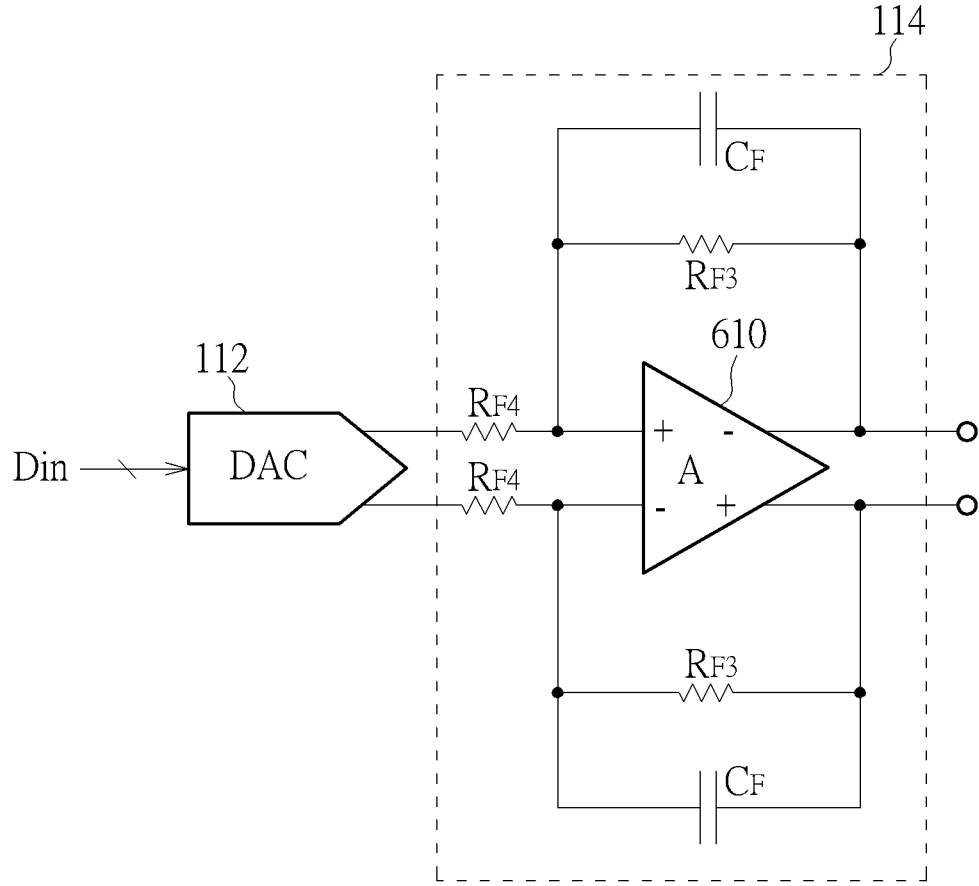
FIG. 6 shows an active filter according to one embodiment of the present invention.

Then, the filter 114 filters the transmitter signal to remove harmonic tones to generate a filtered transmitter signal. FIG. 5 is a diagram illustrating the filter 114 according to one embodiment of the present invention. As shown in FIG. 5, the filter 114 comprises a capacitor $C_{F1}$ and a resistor $R_{F2}$ connected to a first output node of the DAC 112, and the filter 114 further comprises a capacitor $C_{F2}$ and a resistor $R_{F2}$ connected to a second output node of the DAC 112. In the embodiment shown in FIG. 5, the capacitors $C_{F1}$ and $C_{F2}$ are used to remove the high order harmonic tones of the transmitter signal, and the resistors $R_{F1}$ and $R_{F2}$ are used to convert the current signals to voltage signals if the DAC 112 is implemented by the current DAC. FIG. 6 is a diagram illustrating the filter 114 according to another embodiment of the present invention. As shown in FIG. 6, the filter 114 is an active filter comprising input resistors $R_{F4}$, feedback resistors $R_{F3}$, feedback capacitors $C_F$ and an amplifier 610, wherein the input resistors $R_{F4}$ are connected between the DAC 112 and input terminals of the amplifier 610, and the feedback resistors $R_{F3}$ and the feedback capacitors $C_F$ are coupled between the input terminals and output terminals of the amplifier 610.

Then, the filtered transmitter signal is received by the ETI receiver 130 after passing through the capacitors C1 and C2. Then, the ETI receiver 130 receives the filtered transmitter signal to generate the ETI. Specifically, the ETI receiver 130 comprises an in-phase path comprising the first amplifier with mixer 132_1 and the first low-pass filter 134_1, and a quadrature path comprising the second amplifier with mixer 132_2 and the second low-pass filter 134_2. The first amplifier with mixer 132_1 is configured to mix the transmitter signal with an oscillation signal to generate a first mixed signal (low-frequency or DC), then the low-pass filter 134_1 filters the first mixed signal to generate a first filtered signal. The second amplifier with mixer 132_2 is configured to mix the transmitter signal with an oscillation signal to generate a second mixed signal (low-frequency or DC), then the low-pass filter 134_2 filters the second mixed signal to generate a second filtered signal. Then, the first filtered signal and the second filtered signal are processed by the multiplexer 136 and the ADC 138 to generate the ETI. In addition, because the operation of the ETI receiver 130 is known by a person skilled in the art, and the present invention focuses on the ETI transmitter 110, the first capacitor C1 and the second capacitor C2, detailed descriptions of the ETI receiver 130 are omitted here.

Regarding the first capacitor C1 and the second capacitor C2 designed between the input nodes of the biopotential acquisition system 100 and the ETI transmitter 110, the measurement of the ECG will be more accurate and the input range of the input signals $V_{IP}$ and $V_{IN}$ will not become narrower. Specifically, because the first capacitor C1 and the second capacitor C2 have large capacitance under a lower frequency, only a small part of the low-frequency noise generated by the DAC 112 is transmitted to the input node of the biopotential acquisition system 100, that is the input signals $V_{IP}$ and $V_{IN}$ are only slightly affected by the lower-frequency noise generated by the DAC 112. Furthermore, because the first capacitor C1 and the second capacitor C2 have large capacitance under the lower frequency, the input impedance (high impedance) of the ECG receiver 120 will not be influenced due to the ETI transmitter 110. In addition, because the first capacitor C1 and the second capacitor C2 have smaller capacitance under a higher frequency, the filtered transmitter signal can be transmitted to the ETI receiver 130 without excessive loss. Furthermore, because the input nodes of the biopotential acquisition system 100 are connected to the first capacitor C1 and the second capacitor C2, the input signals $V_{IP}$ and $V_{IN}$ have rail-to-rail range, that is the input range of the biopotential acquisition system 100 will not be influenced.

Briefly summarized, in the biopotential acquisition system of the present invention, by designing capacitors between the ETI transmitter and the input nodes of the biopotential acquisition system, the measurement of the ECG signals will not be influenced while the ETI is measured. Therefore, the biopotential acquisition system can accurately measure the ECG signals and ETI at the same time.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A circuitry of a biopotential acquisition system, comprising:
   an input node, configured to receive an input signal from an electrode of the biopotential acquisition system;
   an electrode-tissue impedance (ETI) transmitter, configured to generate a transmitter signal;
   a capacitor, wherein a first node of the capacitor is coupled to the ETI transmitter, and a second node of the capacitor is coupled to the input node; and
   an ETI receiver, coupled to the input node, configured to receive the transmitter signal from the input node to generate an ETI;
   wherein the ETI transmitter comprises:
   a digital-to-analog converter (DAC), configured to receive a digital input signal to generate the transmitter signal; and
   a filter, configured to filter the transmitter signal to generate a filtered transmitter signal to the first node of the capacitor, wherein the input node of the circuitry receives the filtered transmitter signal from the second node of the capacitor.

2. The circuitry of claim 1, wherein the DAC is a current DAC, and the filter filters the transmitter signal and converts the transmitter signal to a voltage signal serving as the filtered transmitter signal.

3. The circuitry of claim 2, wherein the filter comprises:
   a first resistor, coupled between an output node of the DAC and a reference voltage; and
   a first capacitor, coupled between the output node of the DAC and the reference voltage.

4. The circuitry of claim 1, wherein the DAC is a capacitor DAC or a resistor DAC, and the filter filters the transmitter signal to generate the filtered transmitter signal.

5. The circuitry of claim 1, wherein the filter is configured to filter high-order harmonic tones of the transmitter signal.

6. The circuitry of claim 1, wherein the transmitter signal is a voltage signal.

7. The circuitry of claim 1, further comprising:
   an electrocardiography (ECG) receiver, configured to receive the input signal to generate an ECG signal, wherein the ECG receiver and the ETI receiver work at the same time.

8. The circuitry of claim 1, wherein a frequency of the transmitter signal is higher than a frequency of the input signal.

9. The circuitry of claim 1, wherein the filter is an active filter comprising an amplifier with a feedback resistor and a feedback capacitor.

* * * * *